United States Patent [19]

Devine et al.

[11] Patent Number: 5,688,974

[45] Date of Patent: Nov. 18, 1997

[54] PROCESS FOR THE PREPARATION OF AN ENDOTHELIN ANTAGONIST

[75] Inventors: Paul N. Devine, Old Bridge; David M. Tschaen, Holmdel, both of N.J.

[73] Assignee: Merck & Co., Inc., Rahway, N.J.

[21] Appl. No.: 759,690

[22] Filed: Dec. 6, 1996

Related U.S. Application Data

[60] Provisional application No. 60/008,756 Dec. 12, 1995.
[51] Int. Cl.⁶ .................................................. C07D 317/44
[52] U.S. Cl. .................................................. 549/441
[58] Field of Search ..................................... 549/441

[56] References Cited

FOREIGN PATENT DOCUMENTS 0 617 001 A1   9/1994   European Pat. Off. .
WO 96/04905   2/1996   WIPO .
WO 96/08486   3/1996   WIPO .

*Primary Examiner*—Peter O'Sullivan
*Attorney, Agent, or Firm*—Valerie J. Camara; Mark R. Daniel

[57] ABSTRACT

The instant invention relates to a process for the stereoselective synthesis of a compounds of formula I:

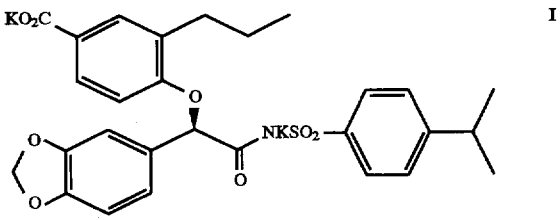

30 Claims, No Drawings

PROCESS FOR THE PREPARATION OF AN ENDOTHELIN ANTAGONIST

This application claims the benefits of U.S. Provisional Application Ser. No. 60/008,756, filed 12 Dec. 1995.

BACKGROUND OF THE INVENTION

Endothelin is a 21-amino acid peptide produced by endothelial cells. The peptide is secreted not only by endothelial cells but also by tracheal epithelial cells or from kidney cells. Endothelin (ET-1) has a potent vasoconstrictor effect. The vasoconstricting effect is caused by the binding of endothelin to its receptor on the vascular smooth muscle cells. [Nature, 332, 411–415 (1988); FEBS Letters, 231, 440–444 (1988); Biochem. Biophys. Res. Commun. 154, 868–875 (1988).]

Endothelin-1 (ET-1) is one of three recently identified potent vasoconstricting peptides which also includes endothelin-2 (ET-2) and endothelin-3 (ET-3) whose sequences differ from ET-1 by two and six amino acids, respectively. [TiPS, 13, 103–108, March 1992.]

Increased levels of endothelin are found in the blood of patients with essential hypertension, acute myocardial infarction, pulmonary hypertension, Raynaud's disease or atherosclerosis or in the washing fluids of the respiratory tract of patients with asthma compared to normal levels. [Japan J. Hypertension 12, 79 (1989); J. Vascular Medicine Biology, 2, 207 (1990); J. Am. Med. Association, 264, 2868 (1990); and The Lancet, ii, 207 (1990) and The Lancet, ii, 747–748 (1989).]

An experimental model of cerebral vasospasm and a second model of acute renal failure have led to the conclusion that endothelin is one of the mediators causing cerebral vasospasm following a subarachnoid hemorrhage, and renal failure. [Japan. Soc. Cereb. Blood Flow & Metabol. 1, 73 (1989); and J. Clin. Invest., 83, 1762–1767 (1989).]

Endothelin was also found to control the release of many physiological substances such as renin, atrial natriuretic peptide, endothelium-derived relaxing factor (EDRF), thromboxane $A_2$, prostacyclin, norepinephrine, angiotensin II and substance P. [Biochem. Biophys. Res. Comm. 157, 1164–1168 (1988); Biochem. Biophys. Res. Comm. 155, 167–172 (1989); Proc. Natl. Acad. Sci. USA, 85, 9797–9800 (1989); J. Cardiovasc. Pharmacol., 13, 589–592 (1989); Japan. J. Hypertension 12, 76 (1989); and Neuroscience Letters, 102, 179–184 (1989).] Further, endothelin causes contraction of the smooth muscle of the gastrointestinal tract and the uterine smooth muscle. [FEBS Letters, 247, 337–340 (1989); Eur. J. Pharmacol. 154, 227–228 (1988); Biochem. Biophys. Res. Commun., 159, 317–323 ( 1989).] Endothelin has also been shown to promote the growth of rat vascular smooth muscle cells which would suggest a possible relevance to arterial hypertrophy. [Atherosclerosis, 78, 225–228 ( 1989).]

Endothelin receptors are present in high concentration in the peripheral tissues and also in the central nervous system, and cerebral administration of endothelin has been shown to induce behavioral changes in animals, suggesting that endothelin may play an important role in controlling neural functions. [Neuroscience Letters, 97, 276–279 ( 1989).]

Endotoxin has been shown to promote the release of endothelin. This finding has suggested that endothelin is an important mediator for endotoxin-induced diseases. [Biochem. Biophys. Res. Commun. 161, 1220–1227 (1989); and Acta. Physiol. Scand., 137, 317–318 (1989).]

A study has shown that cyclosporin added to a renal cell culture, increased endothelin secretion. [Eur. J. Pharmacol., 180, 191–192 (1990).] Another study has shown that administration of cyclosporin to rats, led to a decrease in the glomerular filtration rate and an increase in the blood pressure, in association with a remarkable increase in the circulating endothelin level. This cyclosporin-induced renal failure can be suppressed by the administration of anti-endothelin antibody. [Kidney Int. 37, 1487–1491 (1990).] These studies suggest that endothelin is significantly involved in the pathogenesis of cyclosporin-induced renal disease.

A recent study in patients with congestive heart failure demonstrated a good correlation between the elevated levels of endothelin in the plasma and the severity of the disease. [Mayo Clinic Proc., 67, 719–724 (1992).]

Endothelin is an endogenous substance which directly or indirectly (through the controlled release of various other endogenous substances) induces sustained contraction of vascular or non-vascular smooth muscles. Its excess production or excess secretion is believed to be one of the factors responsible for hypertension, pulmonary hypertension, Raynaud's disease, bronchial asthma, acute renal failure, myocardial infarction, angina pectoris, arteriosclerosis, cerebral vasospasm and cerebral infarction. See A. M. Doherty, *Endothelin: A New Challenge*, J. Med. Chem., 35, 1493–1508 (1992).

Substances which specifically inhibit the binding of endothelin to its receptor are believed to block the physiological effects of endothelin and are useful in treating patients with endothelin related disorders.

The present invention relates to a stereoselective synthesis of the compound

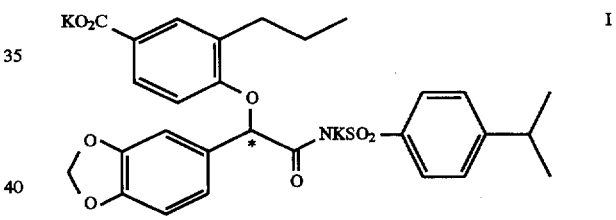

I which is disclosed in PCT International Publication No. WO 94/21590 published on 29 Sep. 1994 by Merck & Co., Inc. The route described previously by Merck & Co., Inc. was a racemic route to this endothelin antagonist. This approach required a classical resolution of a late stage intermediate in order to obtain the desired enantiomer. This was deemed inefficient for large scale synthesis of a potential drug candidate.

SUMMARY OF THE INVENTION

This inventions relates to the stereoselective synthesis of

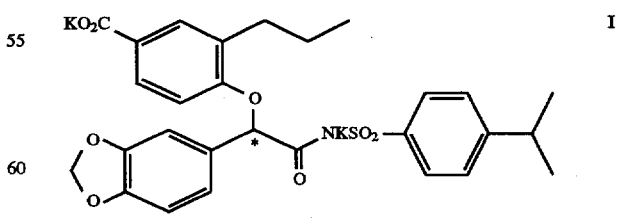

I useful for the large scale preparation of the stereoisomers of this compound. The synthesis involves the use of a chiral auxiliary to enhance the stereoselectivity of the alkylation step. The enantiomeric may be enhanced by recrystallization of a diastereomeric purity of salt.

DETAILED DESCRIPTION OF THE INVENTION

This invention relates to a process for the stereoselective synthesis of

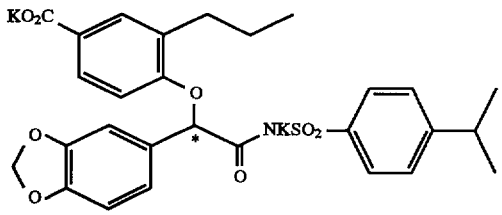

I useful for the large scale preparation of the stereoisomers of this compound.

The instant invention relates to a process for the preparation of a compound of the structural formula I:

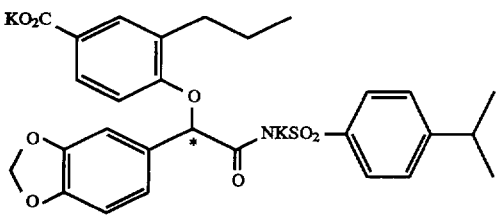

I wherein the * represents a chiral center;
comprising the steps of:

a) reacting the methyl 4-hydroxy-3-n-propylbenzoate with a base in an aprotic solvent to give a salt of methyl 4-hydroxy-3-n-propylbenzoate

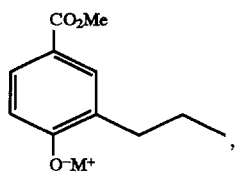

wherein $M^+$ is $Na^+$, $K^+$, or $Li^+$;

b) acylating 1,3-benzodioxole with ethyl oxalyl chloride in the presence of a lewis acid and an organic solvent to give an ester

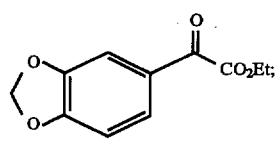

c) hydrolyzing the ester with a base in a solvent to give an acid

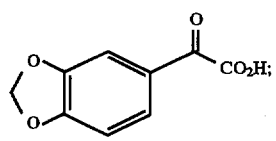

d) reacting the acid with a chlorinating agent in a solvent to give an acid chloride

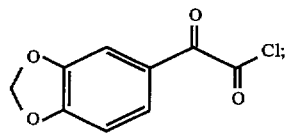

e) reacting the acid chloride with a chiral auxiliary, $R^c$, and an organic base to give a substituted ketoester derivative

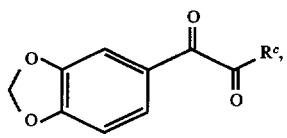

wherein $R^c$ is

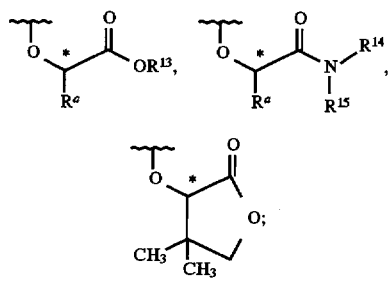

$R^a$ is $(C_1-C_6)$-alkyl, phenyl, or cyclohexyl;

$R^{13}$ is $(C_1-C_6)$-alkyl, phenyl or cyclohexyl;

$R^{14}$ and $R^{15}$ are independently: $(C_1-C_{10})$-alkyl, or $R^{14}$ and $R^{15}$ can join together to form a 5- or 6-membered heterocyclic ring selected from the group consisting of: piperadinyl or pyrrolidinyl;

f) reducing the substituted ketoester derivative with a reducing agent to give a hydroxyl derivative

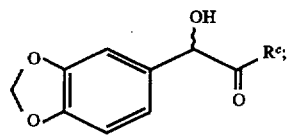

g) halogenating the hydroxyl derivative with a halogenating agent in an organic solvent to give a halo derivative

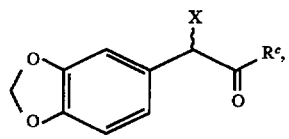

wherein: X is Br, Cl, or I;

h) alkylating the salt of methyl 4-hydroxy-3-n-propylbenzoate with the halo derivative, in an organic solvent to give a chiral auxiliary phenoxyphenylacetic acid derivative

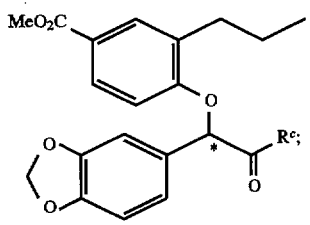

i) hydrolyzing the chiral auxiliary from the phenoxyphenylacetic acid derivative with an inorganic base in an aqueous organic solvent mixture to give a phenoxyphenylacetic acid

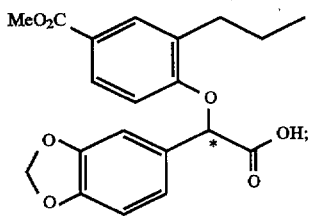

j) reacting the phenoxyphenylacetic acid with a chlorinating agent in a solvent to give an acid chloride

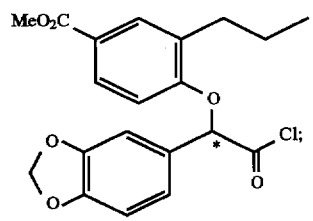

k) reacting the acid chloride with a source of ammonia to give an amide

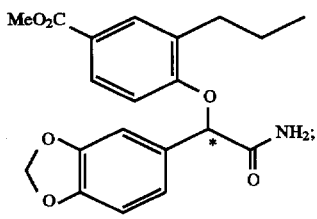

l) alkylating the amide with 4-isopropylbenzenesulfonyl chloride in the presence of a base and a solvent to give a sulfonamide

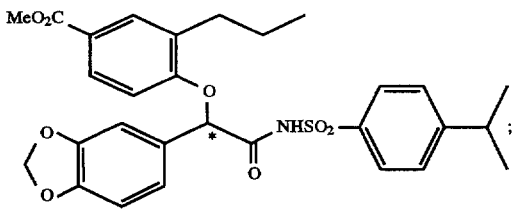

m) hydrolyzing the sulfonamide with an inorganic base in a solvent to give a salt of the acid

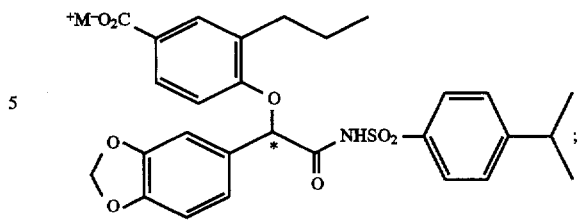

n) neutralizing the salt with mineral acid to give a diacid

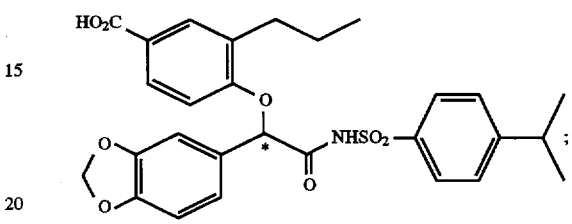

o) reacting the diacid with two equivalents of α-methylbenzylamine in an organic solvent to give a diastereomeric salt

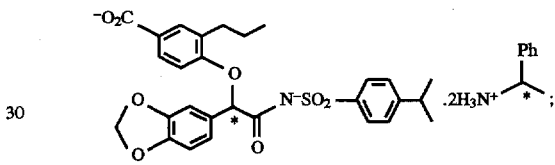

p) breaking the salt with mineral acid to give an optically enriched acid

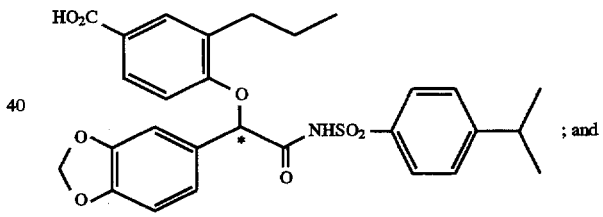

; and q) reacting the optically enriched acid with a base in a solvent or mixture of solvents to give a dipotassium salt, the compound of formula I

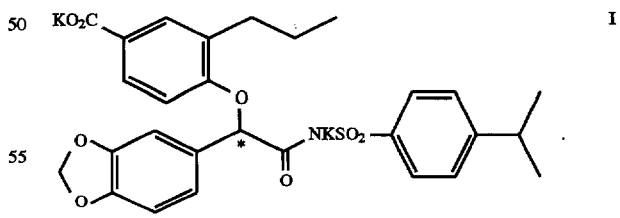

I

The process as recited above, wherein the base in step a is selected from the group consisting of sodium, potassium, or lithium carbonate, sodium, potassium, or lithium t-butoxide, sodium, potassium, or lithium t-amylate, sodium, potassium, or lithium hydroxide, or sodium, potassium, or lithium hydride; and the aprotic solvent in step a is selected from the group consisting of: tetrahydrofuran, toluene and dimethylformamide.

The process as recited above, wherein the Lewis acid in the acylating step b is selected from the group consisting of:

AlCl₃, FeCl₃, TiCl₄, and BF₃-etherate; and the organic solvent in the acylating step b is selected from the group consisting of dichloromethane and dichlorobenzenes.

The process as recited above, wherein the base in the hydrolysis step c is selected from the group consisting of: NaOH, KOH, NaOCH₃, KOCH₃, KOCH₂CH₃, NaOCH₂CH₃, KOt-butyl and NaOt-butyl; and the solvent in the hydrolysis step c is selected from the group consisting of: tetrahydrofuran, methanol, ethanol, t-butanol, dimethylformamide and dimethylsulfoxide.

The process as recited above, wherein the chlorinating agent in step d is selected from the group consisting of: oxalyl chloride, SO₂Cl₂, POCl₃, PCl₃ and PCl₅; and the solvent in step d is selected from the group consisting of: tetrahydrofuran, toluene and dimethylformamide.

The process as recited above, wherein the chiral auxiliary in step e is selected from the group consisting of:

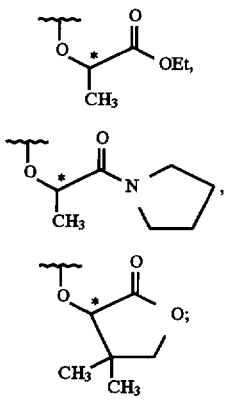

and the organic base in step e is selected from the group consisting of: triethylamine, pyridine and diisopropylethylamine.

The process as recited above, wherein the reducing agent in step f is selected from the group consisting of: NaBH₄, NaCNBH₃ and Na(OAc)₃BH; and the solvent in step f is selected from the group consisting of: tetrahydrofuran-water, ethanol, methanol, dimethylformamide and dimethylsulfoxide.

The process as recited above, wherein the halogenating agent in the halogenation step g is selected from the group consisting of: PBr₃, CBr₄-P(C₆H₅)₃, NBS-DMF, PCl₃, CCl₄-P(C₆H₅)₃ and NCS-DMF; and the organic solvent in the halogenating step is selected from the group consisting of tetrahydrofuran, dichloromethane and toluene.

The process as recited above, wherein the organic solvent in step h is selected from the group consisting of: tetrahydrofuran, toluene and dimethylformamide.

The process as recited above, wherein the inorganic base in the chiral auxiliary hydrolysis step i is selected from the group consisting of: LiOH-H₂O₂, LiOH, KOH or NaOH; and the aqueous organic solvent mixture in the chiral auxiliary hydrolysis step i is selected from the group consisting of: tetrahydrofuran, toluene-water, dimethylformamide, methanol, ethanol and t-butanol.

The process as recited above, wherein the chlorinating agent in the acyl chloride formation step j is selected from the group consisting of: oxalyl chloride, SO₂Cl₂, POCl₃, PCl₃ and PCl₅; and the solvent in step j is selected from the group consisting of: tetrahydrofuran, toluene and dimethylformamide.

The process as recited above, wherein the source of ammonia in step k is selected from the group consisting of:

NH₃(g), aqueous ammonium hydroxide, ammonium chloride-Na₂CO₃ and ammonium chloride-K₂CO₃.

The process as recited above, wherein the base in step 1 is selected from the group consisting of: NaOt-amyl, KOt-amyl, NaOt-butyl, KOt-butyl, NaH, and KH; and the solvent in step 1 is selected from the group consisting of tetrahydrofuran and toluene.

The process as recited above, wherein the inorganic base in step m is selected from the group consisting of: NaOH, KOH and LiOH; and the solvent in step m is selected from the group consisting of: tetrahydrofuran-water.

The process as recited above, wherein the mineral acid in the neutralization step n is selected from HCl, H₂SO₄ and HNO₃.

The process as recited above, wherein the organic solvent in step o is selected from the group consisting of ethyl acetate, isopropyl acetate, methanol, ethanol and t-butanol.

The process as recited above, wherein the mineral acid in the breaking step p is selected from the group consisting of: HCl, H₂SO₄ and HNO₃.

The process as recited above, wherein the base in step q is selected from the group consisting of: KOH, KOCH₃, KOCH₂CH₃ and KOt-butyl; and the solvent in step q is selected from the group consisting of: methanol, ethanol, t-butanol, water, and mixtures therefrom.

The stereogenic center represented in the instant invention using an asterik, is optically enriched in two steps in the instant methodology: 1) the alkylation step using a chiral auxiliary; and 2) a diastereoselective recrystallization. The examples are believed to have the stereochemistry indicated. The chiral auxiliary and the amine salt used will dictate the isomer which will predominate in the alkylation step and the diastereoisomer which will crystallize out.

A chiral auxiliary is defined as an easily removable group chiral group which is attached at a position near the site of alkylation and is capable of influencing the direction of nucleophilic attack. Some of the chiral auxiliaries useful in this method are:

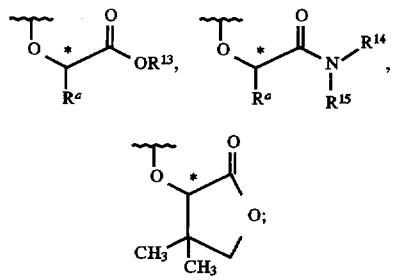

wherein:

Rᵃ is (C₁–C₆)-alkyl, phenyl, or cyclohexyl;

R¹³ is (C₁–C₆)-alkyl, phenyl or cyclohexyl; and

R¹⁴ and R¹⁵ are independently: (C₁–C₁₀)-alkyl, or R¹⁴ and R¹⁵ can join together to form a 5- or 6-membered heterocyclic ring selected from the group consisting of: piperadinyl or pyrrolidinyl.

The preferred chiral auxiliary useful in this invention is when Rᶜ is:

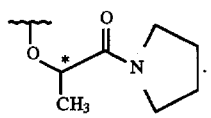

The alkyl substituents recited above denote straight and branched chain hydrocarbons of the length specified such as methyl, ethyl, isopropyl, isobutyl, neopentyl, isopentyl, etc.

The alkenyl-substituents denote alkyl groups as described above which are modified so that each contains a carbon to carbon double bond such as vinyl, allyl and 2-butenyl.

Cycloalkyl denotes rings composed of 3 to 8 methylene groups, each of which may be substituted or unsubstituted with other hydrocarbon substituents, and include for example cyclopropyl, cyclopentyl, cyclohexyl and 4-methylcyclohexyl.

The alkoxy substituent represents an alkyl group as described above attached through an oxygen bridge.

The heteroaryl is defined as carbazolyl, furyl, thienyl, pyrrolyl, isothiazolyl, imidazolyl, isoxazolyl, thiazolyl, oxazolyl, pyrazolyl, pyrazinyl, pyridyl, pyrimidyl, purinyl or quinolinyl.

The synthesis begins with the allylation of readily available methyl-4-hydroxybenzoate (Scheme 1). The allylated phenol is then thermally rearranged in dichlorobenzene and subsequently hydrogenated to provide the desired Methyl-4-hydroxy-3-n-propylbenzoate in good overall yield.

SCHEME 1

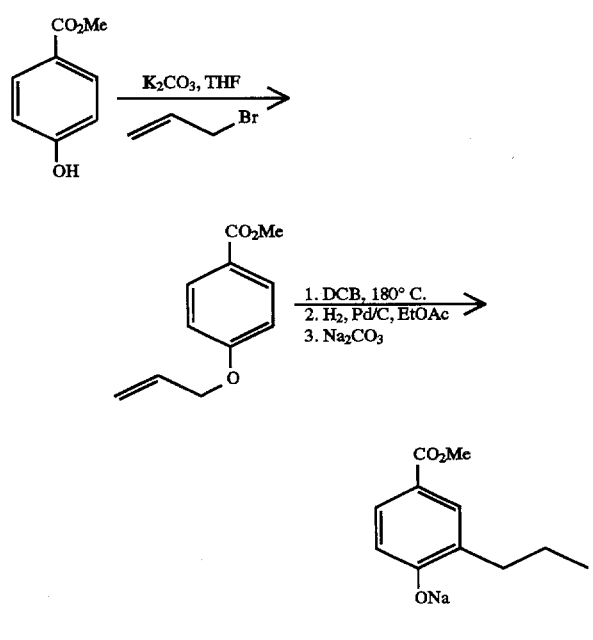

Friedel-Crafts reaction of 1,3-benzodioxole with ethyl oxalyl chloride provides the ketoester 3 in high yield. Without isolation, this intermediate is hydrolyzed to the corresponding ketoacid which can be isolated as a crystalline solid. This acid is then converted via the acid chloride to the (S)-ethyl lactate ester 5 (Scheme 2).

SCHEME 2

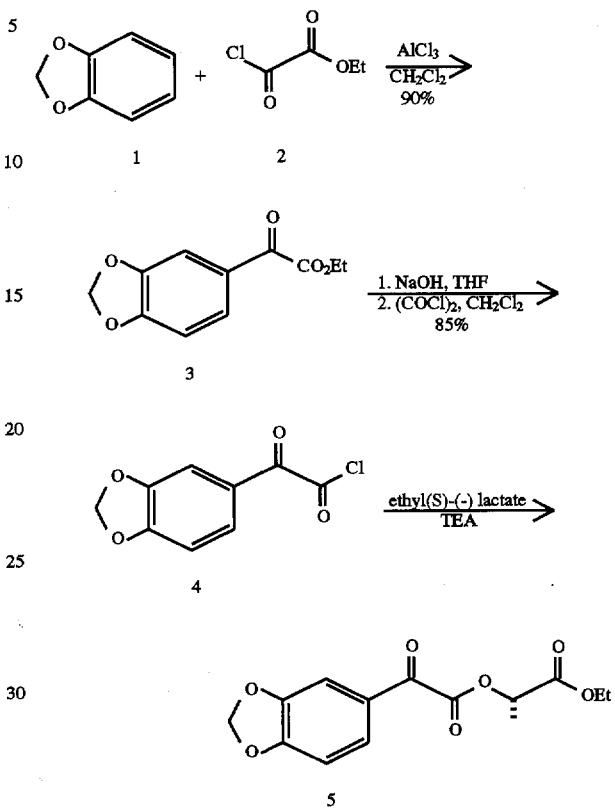

Sodium borohydride reduction of the keto-ester generates a diastereomeric mixture of hydroxyesters 6 (Scheme 3). Ratios as high as 65:35 have been observed. The crude mixture of alcohols is typically converted to a mixture of the corresponding diastereomeric bromides using phosphorous tribromide. The diastereomeric mixture of bromides is not crystalline and is typically carried onto the following step without any purification.

SCHEME 3

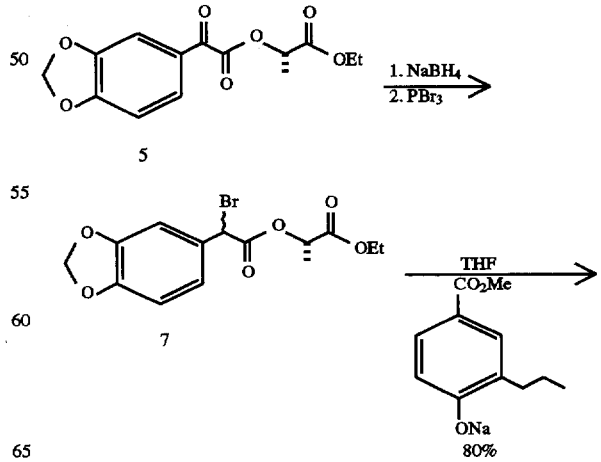

-continued
SCHEME 3

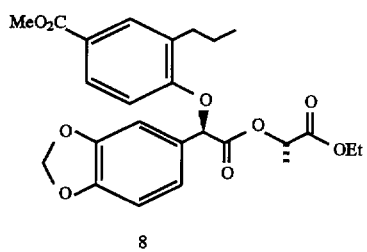

8

The coupling reaction of the sodium salt of methyl-4-hydroxy-3-n-propylbenzoate with the bromide 7 is conducted in THF at −35° C. Under these conditions the reaction requires ~18 h to go to completion and the product is obtained in 80% yield with a diastereomeric ratio of approximately 90:10. Running the reaction at higher temperatures accelerates the rate, however, the diastereoselectivity is lower.

The crude coupling product was treated with lithium hydroperoxide in order to hydrolyze the lactate auxiliary (Scheme 4). Under these conditions, little or no racemization of the chiral center was observed. Saponification using a stronger base such as lithium hyroxide leads to some racemization. Reaction of the crude acid with oxalyl chloride followed by ammonium hydroxide generates the amide which is isolated as a crystalline intermediate. Results indicate that the enantiomeric purity of this compound can be upgraded by recrystallization. The material is typically isolated in 85% yield with an enatiomeric excess of 75–80%.

SCHEME 4

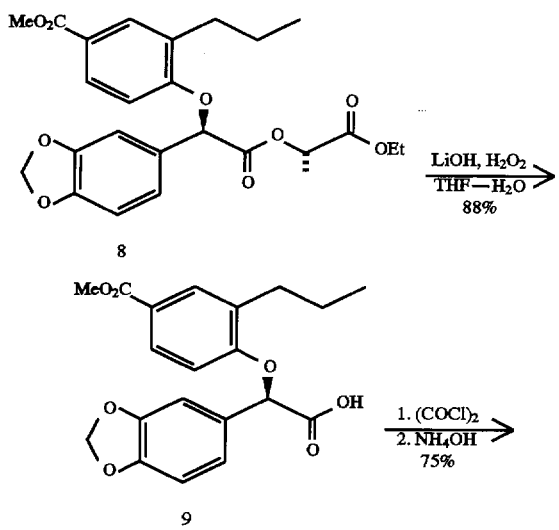

Sulfonylation of the amide using sodium tert-amylate and 4-isopropylbenzenesulfonyl chloride in THF generates the desired product in good yield without racemization (Scheme 5, Ar represents 4-isopropylbenzene). This intermediate is not isolated but typically treated with potassium hydroxide in methanol to hydrolyze the ester. The diacid is then treated with two equivalents of (R)-α-methylbenzylamine to form the diamine salt. This diastereomeric salt precipitates from EtOAc. One recrystallization gives material of greater than 99% ee after salt breaking.

The diamine salt is treated with HCl to liberate the diacid. Diacid 14 is crystallized from methanol and water to provide pure (>99A%, >99% ee) material. Formation of the dipotassium salt of 14 to generate compound I is complicated by the fact that the product forms a variety of different solvates and hydrates. Ultimately, it was found that the MeOH solvate of Compound I crystallized nicely and could be converted to the desired dihydrate through exposure to an atmosphere of moist air.

SCHEME 5

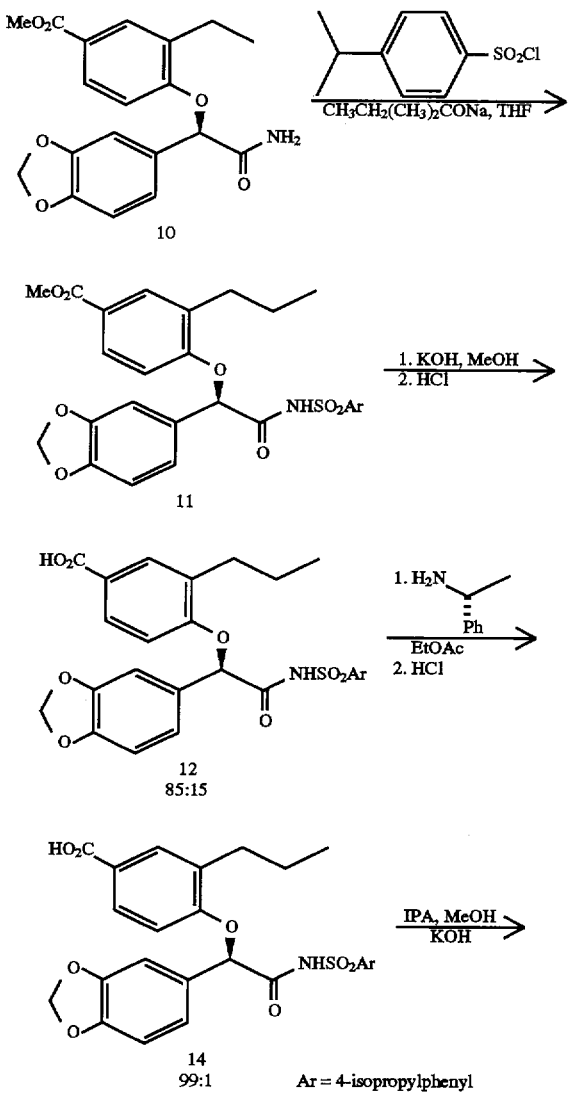

Ar = 4-isopropylphenyl

-continued
SCHEME 5

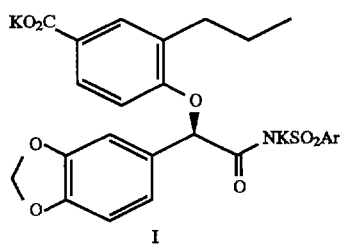

I

The instant invention can be understood further by the following examples, which do not constitute a limitation of the invention.

EXAMPLE 1

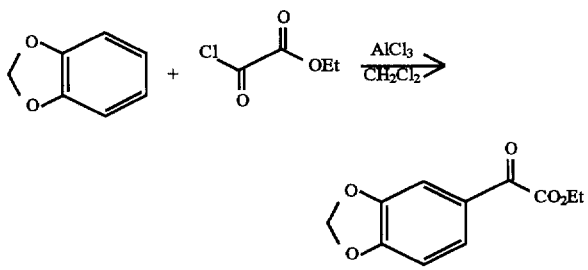

To a slurry of aluminum chloride (150 g, 1.13 mole) in methylene chloride (800 ml) at −55° C. was added ethyl oxalyl chloride (100 ml, 0.89 moles) over 5 min. The reaction exothermed to −48° C. and was cooled back down to −55° C. over 15 min. 1,3-Benzodioxole (100 g, 94 ml, 0.82 moles) was added over 15 min while the reaction temperature was maintained between −45° C. and −55° C. using dry ice/acetone. The red solution was aged for 20 min. The batch was carefully quenched into 700 ml of ice water and the mixture agitated for 10 min. The layers were separated and the organic layer was washed with water (500 ml). Concentration in vacuo provided the product as a brown oil (184 g) which was used in the next step without purification.

EXAMPLE 2

Synthesis of Ketoacid

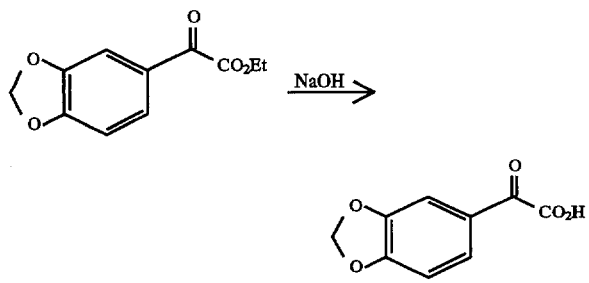

To a solution of ketoester 3 (182 g, 0.82 mole) in methanol (800 ml) was added a mixture of 5N sodium hydroxide (300 ml) and water (300 ml) while maintaining the temperature below 35° C. using an ice bath. The batch was aged for 20 min. during which time a precipitate formed. Methylene chloride (500 ml) was added and the mixture was acidified to pH 3.0 using concentrated HCl. The layers were separated and the organic phase was concentrated in vacuo to 100 ml. Toluene (300 ml) was added and concentration was continued to a final volume of 300 ml. The resulting slurry was aged for 1 h and filtered. The wet cake was washed with hexane and air dried to provide 120 g of ketoacid as a tan solid.

EXAMPLE 3

Lactate Ester Formation

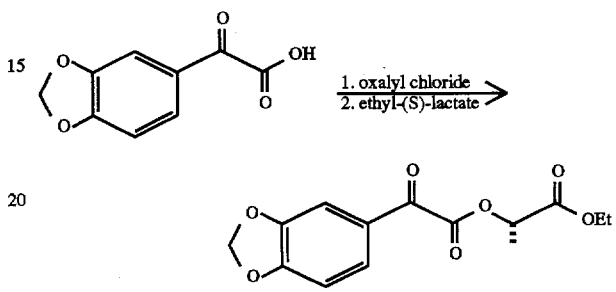

To a slurry of ketoacid (80 g, 0.41 moles) in methylene chloride (800 ml) at 20°–25° C. was added DMF (3 ml). Oxalyl chloride (37 ml, 0.42 moles, d=1.45 g/ml) was added over 10 min.

Within 20 min the reaction mixture turned to a clear solution. NMR assay of a small sample indicated <5% ketoacid remaining. The reaction mixture was then added via cannula over 15 min to a solution of ethyl-(S)-lactate (44 ml, 0.39 mole, d=1.042 g/ml), and TEA (143 ml, d=0.72 g/ml) in methylene chloride (600 ml) while maintaining the temperature <30° C. using an ice bath. The mixture was aged for 1 h. The batch was quenched into water (500 ml) and the layers separated. The organic layer was washed with water (500 ml) and then with sat'd sodium bicarbonate (2×300 ml). Concentration in vacuo provided 100 g of product as an oil. The material is used in the next step without purification.

EXAMPLE 4

Lactate Ester Reduction

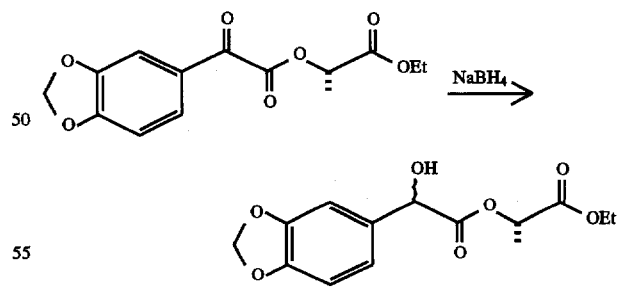

To a solution of lactate ester (100 g, 0.34 mole) in THF (600 ml) at 10°–15° C. was added water (65 ml). Sodium borohydride (5 g, 0.14 mole) was added in 5 portions over 25 min.

The addition of the sodium borohydride was moderately exothermic. The reaction temperature was maintained <25° C. using an ice bath.

The mixture was aged for 20 min and poured into brine (300 ml) and ethyl acetate (600 ml). The layers were cut and the aqueous was back extracted with ethyl acetate (300 ml). The combined organic extracts were washed with water (200 ml) and the layers were separated. Concentration in vacuo yielded 100 g of product as an oil which was used in the next step without purification.

EXAMPLE 5

Preparation of Bromide

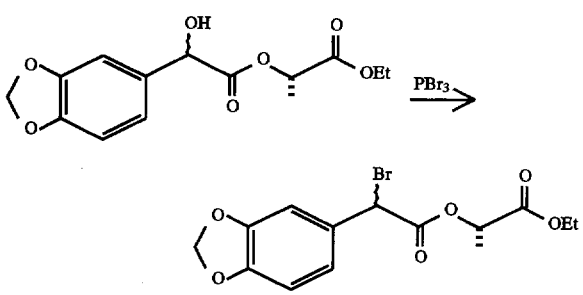

To a solution of the hydroxyester (100 g, 0.34 mole) in methylene chloride (500 ml) at 10°–15° C. was added phosphorous tribromide (12.8 ml, 0.13 moles, d=2.85 g/ml) over 5 min.

The mixture was allowed to warm to 20° C. and aged for 1.5 h. The batch was quenched into water (250 ml) and the organic layer was washed with aqueous sodium bicarbonate (250 ml). Concentration of the organic layer in vacuo provided 111 g of bromide as a dark oil which was used in the next step without purification.

EXAMPLE 6

Phenoxide Coupling

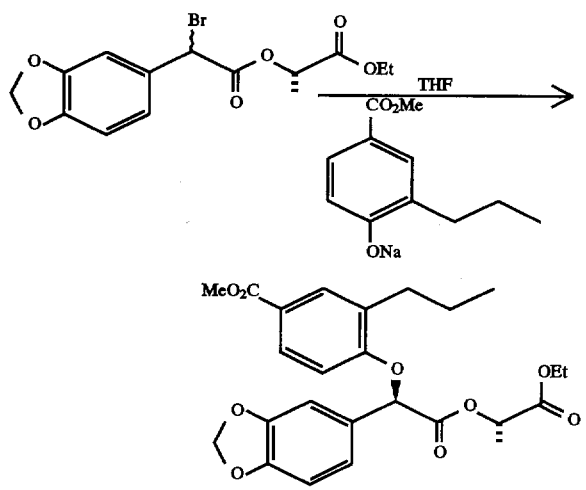

To a solution of methyl 4-hydroxy-3-n-propylbenzoate (23.7 g, 0.12 mole) in THF (175 ml) at 5°–10° C. was added sodium t-butoxide (11.7 g, 0.12 mole) in 3 portions over 15 min while maintaining the temperature <20° C. using an ice bath.

The mixture was aged for 20 min and then added via a cannula to a solution of the bromide (55.0 g, 0.15 mole) in THF (400 ml) at −35° C. The reaction was aged at −35 ° C. for 20 h. The mixture was poured into a mixture of brine (200 ml), water (200 ml), and ethyl acetate (400 ml). The layers were cut and the organic layer was concentrated in vacuo to yield 69.0 g of product as an oil.

The product was isolated as a 90:10 mixture of diastereomers, determined by HPLC.

HPLC assay: Column: Zorbax Rx-C8 4.6 mm×25 cm; solvent: $CH_3CN:H_2O(0.1\%\ H_3PO_4)$ 60:40; flow rate: 1 ml/min; wavelength: 220 nm; column temperature: 25° C.; retention time: major isomer, 20.2 min.; minor isomer 18.8 min.; and bromide, 7.8 min.

EXAMPLE 7

Lactate Ester Hydrolysis

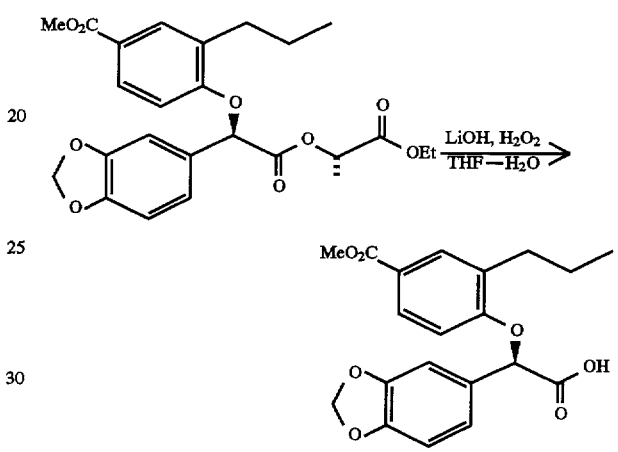

Hydrogen peroxide (3.5 1, 133.8 mole) was added to a solution of lithium hydroxide (709 g, 16.9 mole) in water (3.5 1) and the mixture was aged for 20 min at 20°–25° C. This solution was then slowly added over 30 min to a cold (0°–5° C.) solution of lactate ester 8 (3.1 kg, 6.76 mole) in THF (28 1).

The reaction mixture was aged for 30 min, cooled to 0°–5° C. and quenched with sat'd aqueous sodium bisulfite (6 1).

Sat'd aqueous ammonium chloride (4 1) and methyl t-buthyl ether (36 1) was added and after agitation the layers were separated.

The organic layer was dried over $MgSO_4$ (1 kg) and then concentrated in vacuo to yield 2.6 kg of crude product as a dark oil which was used without futher purification.

EXAMPLE 8

Preparation of Amide 10

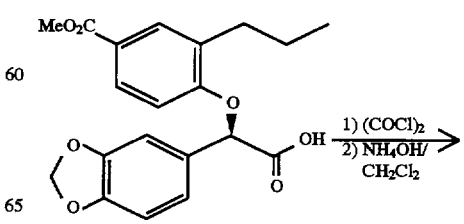

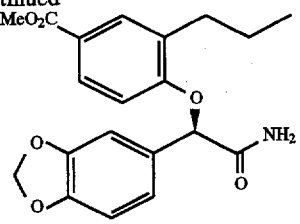

To a solution of the acid 9 (725 g, 1.9 mole) in methylene chloride (9 l) at 20° C. was added DMF (20 ml). Oxalyl chloride (203 ml, 2.38 mole, d=1.45 g/ml) was added over 20 min and the mixture was aged for 60 min. Gas evolution was evident during the addition and continued throughout the reaction. The acid chloride solution was then slowly transfered over 20 min into a cold (0°–5° C.) mixture of ammonium hydroxide (2.6 l), water (3 l) and methylene chloride (10 l).

The layers were separated and the organic phase was concentrated in vacuo and the residual dichloromethane was displaced with methanol. The final volume of methanol was 5 l. Water (5 l) was added over 2 h at 20° C. and the slurry was aged for 30 min. Crystallization initiated after 2 l of water had been added. The product was isolated by filtration and the cake was washed with water (1 l). Drying under a nitrogen sweep yielded 606 g of an off-white solid. HPLC assay of the product indicated an 88:12 mixture of diastereomers.

HPLC assay: Column: Zorbax Rx-C8 4.6 mm×25 cm; solvent: $CH_3CN:H_2O(0.1\% \ H_3PO_4)$ 60:40; flow rate: 1 ml/min; wavelength: 220 nm; column temperature: 25° C.; retention time: product, 5.6 min.; statring material, 6.9 min.

Chiral HPLC assay: Column: Regis (R,R) -Whelk -O 4.6 mm×250 mm; solvent: hexane:isopropylalcohol (0.5% HOAc) 30:70; flow rate: 1 ml/min; wavelength: 220 nm; column temperature: 25° C.; retention time: minor isomer, 6.74 min.; major isomer 19.84 min.

EXAMPLE 9

Sulfonylation of Amide

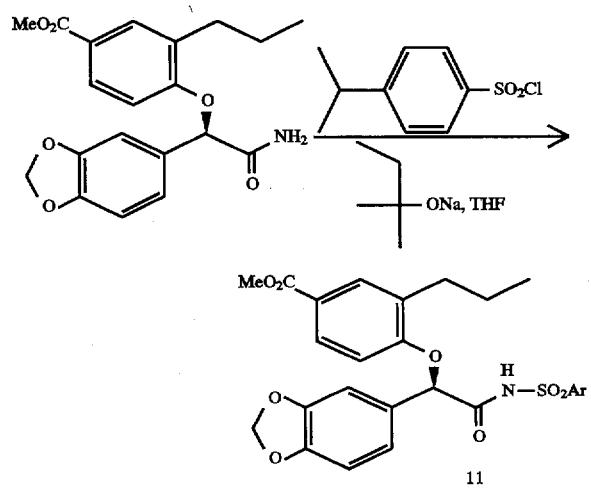

To a solution of amide (578 g, 1.56 moles) and 4-isopropylbenzenesulfonyl chloride (409 g, 1.9 moles) in THF (6 l) at 0°–5° C. was added a solution of sodium t-amylate (378 g, 3.43 moles) in THF (3 l) over a 1 h period. The temperature was maintained at 0°–5° C. by controlling the rate of addition and by using an external cooling bath. The mixture was aged for 0.5 h and quenched with sat'd aqueous ammonium chloride (3 l) and water (3.5 l). Methylene chloride (18 l) was added and the phases were separated. Concentration of the organic phase in vacuo yielded the product as a dark oil which was used without purification.

EXAMPLE 10

Methyl Ester Hydrolysis

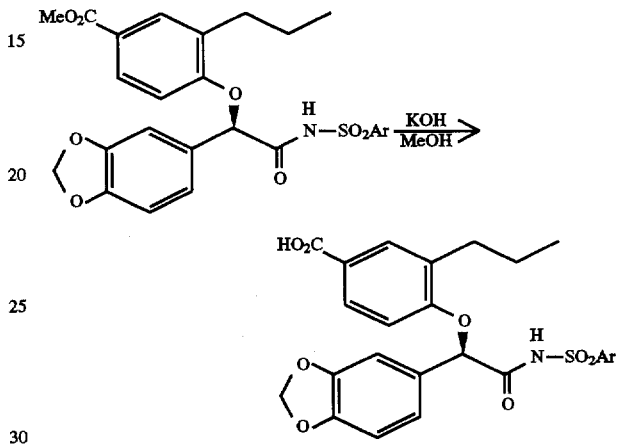

To a solution of the methyl ester (862 g, 1.56 mole) in methanol (5 l) was added 2N KOH (2 l). The mixture was heated to reflux for 1.5 h. The mixture was cooled to 25° C. and quenched into a mixture of 1N HCl (9 l) and methylene chloride (10 l). The phases were separated and the organic phases was concentrated in vacuo to provide 615 g of product as a dark oil.

EXAMPLE 11

Diamine Salt Formation and Recrystalization

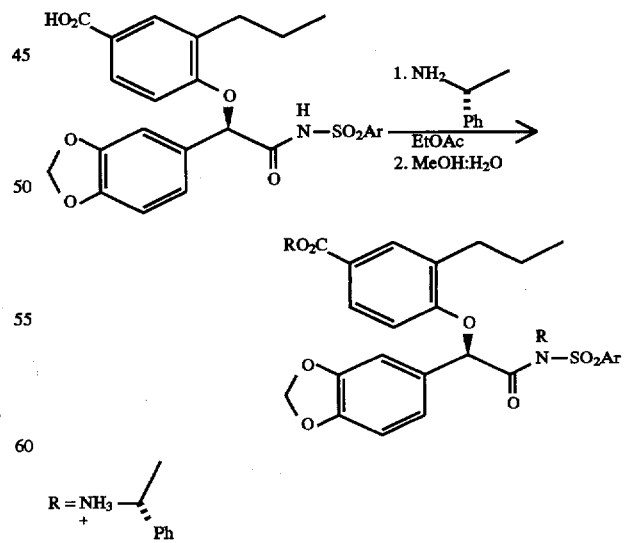

To a solution of the acid (615 g, 1.14 moles) in ethyl acetate (11 l) was added (R)-(2)-methylbenzylamine (350 ml, 2.71 moles) in one portion. The solution was seeded with 5 g of diamine salt and the mixture was aged for 16 h. The resulting slurry was filtered and the cake was dried under a nitrogen sweep for 18 h to provide 800 g of the diamine salt as an off-white solid. HPLC assay of the material on an (R,R)-Whelk-O column eluting with IPA/hexane 50:50 (0.5% HOAc) indicated 93% ee. The diamine salt (800 g) was dissolved in methanol (7 l) and water (6 l) was added over 30 min. Methanol (1.5 l) was removed by vacuum distillation at 20°–30° C. and water (5 l) was added to the resulting slurry over 30 min. The slurry was aged for 30 min and filtered. The product was dried under a nitrogen sweep for 18 h to provide 430 g of product as a off-white solid. HPLC assay under the same conditions indicated >99% ee.

EXAMPLE 12

Dissociation of the Diamine Salt

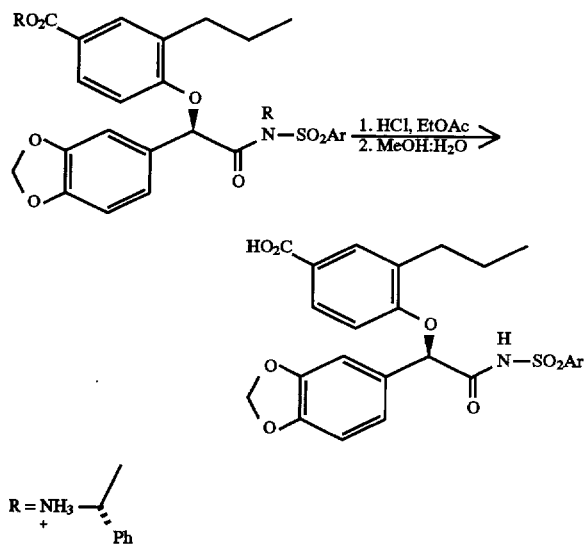

To a mixture of ethyl acetate (15 l) and 1N HCl (10 l) was added diamine salt (837 g, 1.07 mole). The mixture was agitated for 20 min and the layers were settled. The organic layer was treated with Darco KB (60 g) for 1 h and then filtered through Celite to remove the carbon. The ethyl acetate solution was concentrated in vacuo to an oil which was dissolved in methanol (6 l). Water (1.5 l) was added over 30 min. at 20° C. and an additional 1.5 l of water was then added (30 min) to the resulting slurry. After a 30 min age the batch was filtered and the cake was washed with MeOH: Water (1 l of 50:50). The product was dried for 16 h under a nitrogen sweep to yield 495 g of product as a white solid. HPLC assay indicated the material to be >99 A% pure. Chiral HPLC assay indicated the material to be >99% ee.

Chiral HPLC assay: Column: Regis (R,R) -Whelk -O 4.6 mm×250 mm; solvent: hexane:isopropylalcohol (0.5% HOAc) 50:50; flow rate: 1 ml/min; wavelength: 220 nm; column temperature: 25° C.; retention time: minor isomer, 7.9 min.; major isomer 10.5 min.

EXAMPLE 13

Synthesis of Compound I

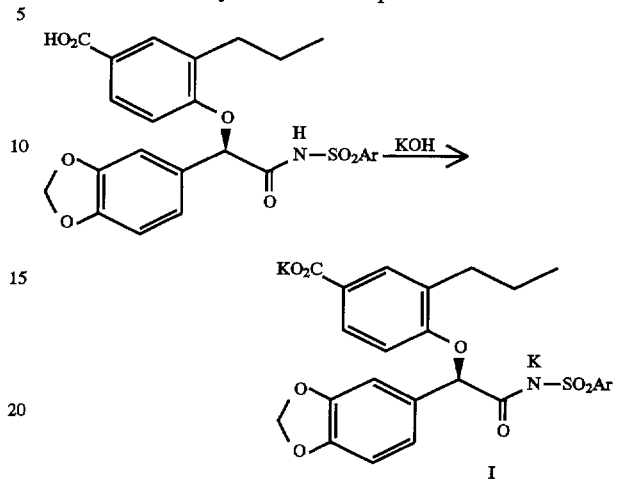

A suspension of diacid (451.5 g, 0.84 mole) in IPA (6.3 l) and MeOH (903 ml) was heated to 45° C. to form a clear solution. To this solution was added a KOH solution (1.9 l of a 0.97M solution in IPA) over 15 min while the temperature was maintained 45°–50° C. The clear solution was slowly cooled over 1 h to 20° C. Crystallization spontaneously initiates at ~42° C. The batch was aged at 20° C. for 2 h and filtered. The cake was washed with IPA (1.0 l) and dried under a nitrogen sweep for 8 h. NMR and TGA indicated the presence of ~5.6% MeOH. The methanol was removed and the cake hydrated by sweeping moist air through the batch for 1.5 h. to provide 490 g of compound I as a white solid. NMR and TGA at this point indicated no MeOH. TGA and KF indicated ~5.7% water.

Chiral HPLC assay: Column: Regis (R,R) -Whelk -O 4.6 mm×250 mm; solvent: hexane:isopropylalcohol (0.5% HOAc) 50:50; flow rate: 1 ml/min; wavelength: 220 nm; column temperature: 25° C.; retention time: minor isomer, 7.9 min.; major isomer 10.5 min.

What is claimed is:

1. A process for the preparation of a compound of the structural formula I:

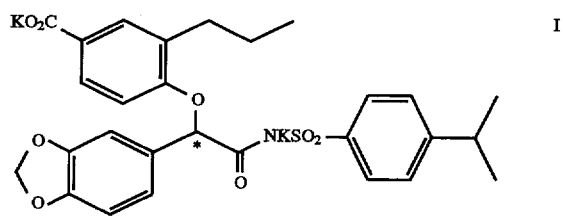

wherein the * represents a chiral center;

comprising the steps of:

a) reacting the methyl 4-hydroxy-3-n-propylbenzoate with a base in an aprotic solvent to give a salt of methyl 4-hydroxy-3-n-propylbenzoate

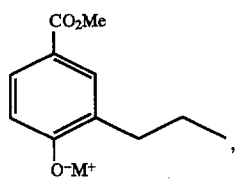

wherein: $M^+$ is $Na^+$, $K^+$, or $Li^+$;

b) acylating 1,3-benzodioxole with ethyl oxalyl chloride in the presence of a lewis acid and an organic solvent to give an ester

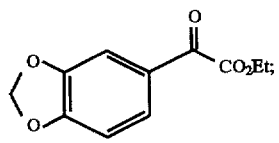

c) hydrolyzing the ester with a base in a solvent to give an acid

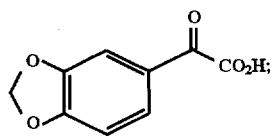

d) reacting the acid with a chlorinating agent in a solvent to give an acid chloride

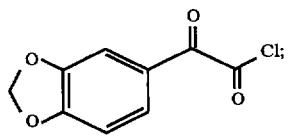

e) reacting the acid chloride with a chiral auxiliary, $R^c$, and an organic base to give a substituted ketoester derivative

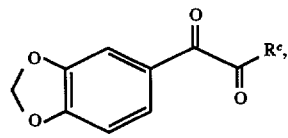

wherein: $R^c$ is

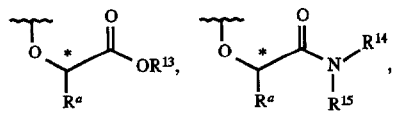

$R^a$ is $(C_1-C_6)$-alkyl, phenyl, or cyclohexyl;
$R^{13}$ is $(C_1-C_6)$-alkyl, phenyl or cyclohexyl;
$R^{14}$ and $R^{15}$ are independently: $(C_1-C_{10})$-alkyl, or $R^{14}$ and $R^{15}$ can join together to form a 5- or 6-membered heterocyclic ring selected from the group consisting of: piperadinyl or pyrrolidinyl;

f) reducing the substituted ketoester derivative with a reducing agent to give a hydroxyl derivative

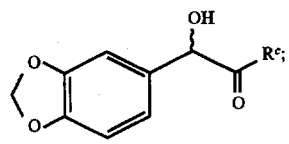

g) halogenating the hydroxyl derivative with a halogenating agent in an organic solvent to give a halo derivative

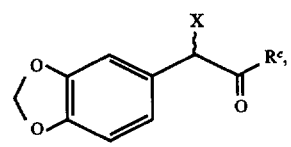

wherein: X is Br, Cl, or I;

h) alkylating the salt of methyl 4-hydroxy-3-n-propylbenzoate with the halo derivative, in an organic solvent to give a chiral auxiliary phenoxyphenylacetic acid derivative

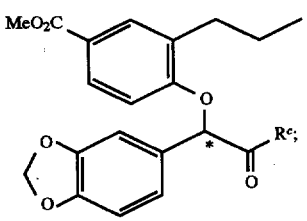

i) hydrolyzing the chiral auxiliary from the phenoxyphenylacetic acid derivative with an inorganic base in an aqueous organic solvent mixture to give a phenoxyphenylacetic acid

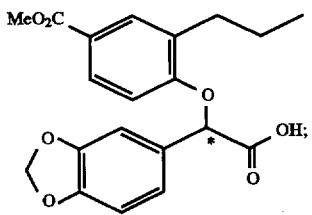

j) reacting the phenoxyphenylacetic acid with a chlorinating agent in a solvent to give an acid chloride

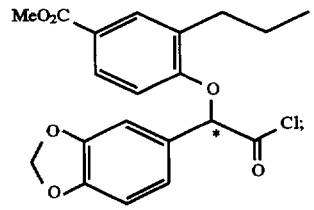

k) reacting the acid chloride with a source of ammonia to give an amide

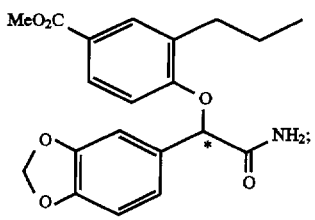

l) alkylating the amide with 4-isopropylbenzenesulfonyl chloride in the presence of a base and a solvent to give a sulfonamide

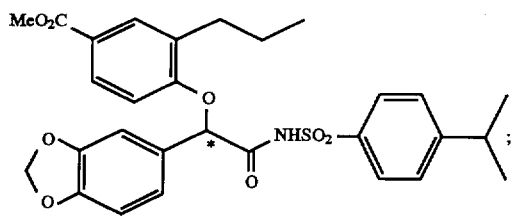

m) hydrolyzing the sulfonamide with an inorganic base in a solvent to give a salt of the acid

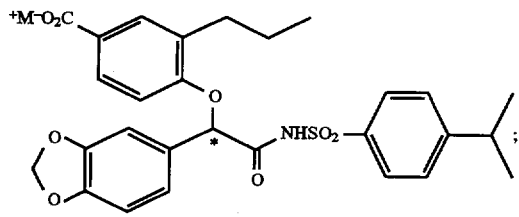

n) neutralizing the salt with mineral acid to give a diacid

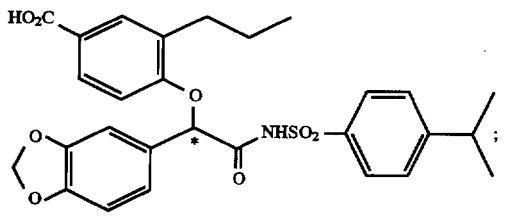

o) reacting the diacid with two equivalents of α-methylbenzylamine in an organic solvent to give a diastereomeric salt

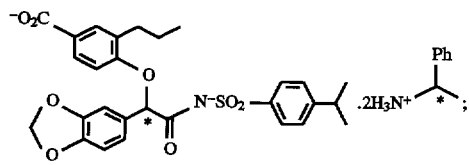

p) breaking the salt with mineral acid to give an optically enriched acid

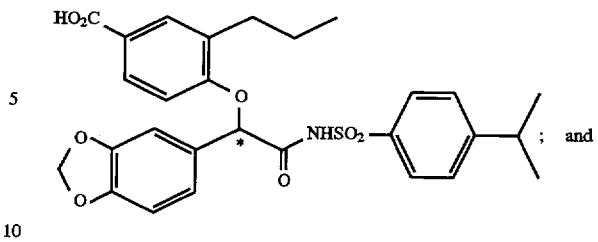

q) reacting the optically enriched acid with a base in a solvent or mixture of solvents to give a dipotassium salt, the compound of formula I

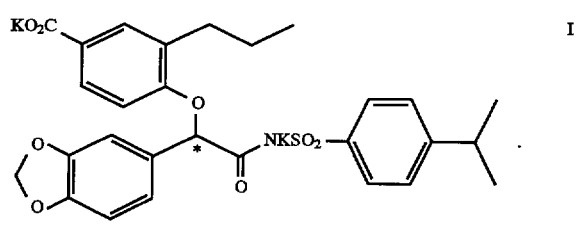

2. The process as recited in claim 1, wherein the base in step a is selected from the group consisting of: sodium, potassium, or lithium carbonate, sodium, potassium, or lithium t-butoxide, sodium, potassium, or lithium t-amylate, sodium, potassium, or lithium hydroxide, or sodium, potassium, or lithium hydride.

3. The process as recited in claim 2, wherein the aprotic solvent in step a is selected from the group consisting of: tetrahydrofuran, toluene and dimethylformamide.

4. The process as recited in claim 3, wherein the Lewis acid in the acylation step b is selected from the group consisting of: $AlCl_3$, $FeCl_3$, $TiCl_4$, and $BF_3$-etherate.

5. The process as recited in claim 4, wherein the organic solvent in the acylation step b is selected from the group consisting of dichloromethane and dichlorobenzenes.

6. The process as recited in claim 5, wherein the base in the hydrolysis step c is selected from the group consisting of: $NaOH$, $KOH$, $NaOCH_3$, $KOCH_3$, $KOCH_2CH_3$, $NaOCH_2CH_3$, KOt-butyl and NaOt-butyl.

7. The process as recited in claim 6, wherein the solvent in the hydrolysis step c is selected from the group consisting of: tetrahydrofuran, methanol, ethanol, t-butanol, dimethylformamide and dimethylsulfoxide.

8. The process as recited in claim 7, wherein the chlorinating agent in step d is selected from the group consisting of: oxalyl chloride, $SO_2Cl_2$, $POCl_3$, $PCl_3$ and $PCl_5$.

9. The process as recited in claim 8, wherein the solvent in step d is selected from the group consisting of tetrahydrofuran, toluene and dimethylformamide.

10. The process as recited in claim 9, wherein the chiral auxiliary in step e is selected from the group consisting of:

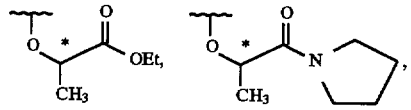

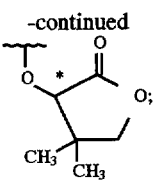

11. The process as recited in claim 10, wherein the organic base in step e is selected from the group consisting of: triethylamine, pyridine and diisopropylethylamine.

12. The process as recited in claim 11, wherein the reducing agent in step f is selected from the group consisting of: $NaBH_4$, $NaCNBH_3$ and $Na(OAc)_3BH$.

13. The process as recited in claim 12, wherein the solvent in step f is selected from the group consisting of: tetrahydrofuran-water, ethanol, methanol, dimethylformamide and dimethylsulfoxide.

14. The process as recited in claim 13, wherein the halogenating agent in the halogenation step g is selected from the group consisting of: $PBr_3$, $CBr_4$-$P(C_6H_5)_3$, NBS-DMF, $PCl_3$, $CCl_4$-$P(C_6H_5)_3$ and NCS-DMF.

15. The process as recited in claim 14, wherein the organic solvent in the halogenating step g is selected from the group consisting of tetrahydrofuran, dichloromethane and toluene.

16. The process as recited in claim 15, wherein the organic solvent in step h is tetrahydrofuran, toluene and dimethylformamide.

17. The process as recited in claim 16, wherein the inorganic base in the chiral auxiliary hydrolysis step i is selected from the group consisting of: LiOH-$H_2O_2$, LiOH, KOH or NaOH.

18. The process as recited in claim 17, wherein the aqueous organic solvent mixture in the chiral auxiliary hydrolysis step i is selected from the group consisting of: tetrahydrofuran, toluene-water, dimethylformamide, methanol, ethanol and t-butanol.

19. The process as recited in claim 18, wherein the chlorinating agent in step j is selected from the group consisting of: oxalyl chloride, $SO_2Cl_2$, $POCl_3$, $PCl_3$ and $PCl_5$.

20. The process as recited in claim 19, wherein the solvent in step j is selected from the group consisting of tetrahydrofuran, toluene and dimethylformamide.

21. The process as recited in claim 20, wherein the source of ammonia in step k is selected from the group consisting of: $NH_3(g)$, aqueous ammonium hydroxide, ammonium chloride-$Na_2CO_3$ and ammonium chloride-$K_2CO_3$.

22. The process as recited in claim 21, wherein the base in step l is selected from the group consisting of: NaOt-amyl, KOt-amyl, NaOt-butyl, KOt-butyl, NaH, and KH.

23. The process as recited in claim 22, wherein the solvent in step l is selected from the group consisting of tetrahydrofuran and toluene.

24. The process as recited in claim 23, wherein the inorganic base in step m is selected from the group consisting of: NaOH, KOH and LiOH.

25. The process as recited in claim 24 wherein the solvent in step m is selected from the group consisting of: tetrahydrofuran-water.

26. The process as recited in claim 25, wherein the mineral acid in the neutralization step n is selected from HCl, $H_2SO_4$ and $HNO_3$.

27. The process as recited in claim 26, wherein the organic solvent in step o is selected from the group consisting of ethyl acetate, isopropyl acetate, methanol, ethanol and t-butanol.

28. The process as recited in claim 27, wherein the mineral acid in the breaking step p is selected from the group consisting of: HCl, $H_2SO_4$ and $HNO_3$.

29. The process as recited in claim 28, wherein the base in step q is selected from the group consisting of: KOH, $KOCH_3$, $KOCH_2CH_3$ and KOt-butyl.

30. The process as recited in claim 29, wherein the solvent in step q is selected from the group consisting of: methanol, ethanol, t-butanol, water, and mixtures therefrom.

* * * * *